(12) United States Patent
Majumdar et al.

(10) Patent No.: US 11,004,540 B2
(45) Date of Patent: May 11, 2021

(54) DETERMINING THE LIMIT OF DETECTION OF RARE TARGETS USING DIGITAL PCR

(71) Applicant: LIFE TECHNOLOGIES CORPORATION, Carlsbad, CA (US)

(72) Inventors: Nivedita Sumi Majumdar, San Bruno, CA (US); Thomas Wessel, Pleasanton, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 598 days.

(21) Appl. No.: 15/579,407

(22) PCT Filed: Jun. 3, 2016

(86) PCT No.: PCT/US2016/035870
§ 371 (c)(1),
(2) Date: Dec. 4, 2017

(87) PCT Pub. No.: WO2016/197028
PCT Pub. Date: Dec. 8, 2016

(65) Prior Publication Data
US 2018/0144094 A1    May 24, 2018

Related U.S. Application Data

(60) Provisional application No. 62/171,855, filed on Jun. 5, 2015.

(51) Int. Cl.
*G16B 40/00* (2019.01)
*G06N 7/00* (2006.01)

(52) U.S. Cl.
CPC ............. *G16B 40/00* (2019.02); *G06N 7/005* (2013.01)

(58) Field of Classification Search
CPC .... C12Q 1/6806; C12Q 1/686; C12Q 1/6851; C12Q 2537/165; C12Q 1/06; C12Q 1/682;
(Continued)

(56) References Cited

U.S. PATENT DOCUMENTS 8,572,506 B2    10/2013   Janaway et al.
9,856,525 B2 *  1/2018    McCoy ............... C12Q 1/6851
(Continued)

FOREIGN PATENT DOCUMENTS

WO      2014074735 A2    5/2014

OTHER PUBLICATIONS

Dreo et al. Optimising droplet digital PCR analysis approaches for detection and quantification of bacteria: a case study of fire blight and brown potato rot. Analytical Bioanalytical Chemistry (2014) 406: 6513-6528.*
(Continued)

*Primary Examiner* — Mary K Zeman
(74) *Attorney, Agent, or Firm* — Jones Robb, P.L.L.C.

(57) ABSTRACT

A method for determining false positives calls in a biological data plot is provided. The method includes identifying a first data cluster as non-amplification data points within the biological data plot and identifying a second data cluster as wild-type positives within the biological data plot. The method further includes estimating a position in the biological data plot of a center of the first and second data clusters. The method further includes determining, for each data point within the first data cluster, a probability of belonging to the first data cluster and determining, for each data point within the second data cluster, a probability of belonging to the second data cluster. The method includes applying a probability threshold for each data point within the first and second data cluster to identify false positives.

18 Claims, 12 Drawing Sheets

(58) Field of Classification Search
CPC ............ C12Q 2537/143; C12Q 1/6848; C12Q 1/6809; C12Q 1/6858; C12Q 2600/156; C12Q 2563/159; C12Q 2531/113; C12Q 2545/114; C12Q 1/68; C12Q 2563/107; C12Q 1/6825; C12Q 1/6816; C12Q 1/6827; C12Q 1/6837; C40B 50/06; C40B 40/08; C40B 70/00; C40B 20/04; C40B 30/04; C40B 40/02; C40B 40/06; C40B 50/16; C40B 50/18; C40B 60/12; G16H 50/20; G16H 10/20; G16H 10/40; G16H 15/00; G16H 20/10; G16H 40/63; G16H 50/30; G16H 50/50; G06F 19/34; G06F 19/00; G06K 19/06028; G06K 19/06093; G06T 7/0012; G06T 11/206; G16B 20/00; G16B 30/00; G16B 30/10; G16B 40/00; G16B 20/20; G16B 25/00; G16B 25/10; G16B 35/00; G16B 40/10; G16B 45/00; G16B 50/00; G16B 99/00; G16B 20/10; G16B 15/00; G16B 25/20; G16B 40/20; G16B 50/50; C12N 15/1003; G06N 7/005; G06N 20/00; B01L 3/502784; G01N 21/6428; G01N 1/38; G01N 2001/2893; G01N 2021/6439; G01N 2201/127; G01N 2021/6441; G01N 33/54386; G01N 2015/1486

See application file for complete search history.

(56) References Cited

U.S. PATENT DOCUMENTS

| | | |
|---|---|---|
| 2002/0067358 A1 | 6/2002 | Casari et al. |
| 2004/0033601 A1 | 2/2004 | Davidson |
| 2005/0019792 A1 | 1/2005 | McBride et al. |
| 2005/0119534 A1 | 6/2005 | Trost et al. |
| 2007/0255506 A1 | 11/2007 | Lobban et al. |
| 2008/0168151 A1 | 7/2008 | Fuchs et al. |
| 2010/0191678 A1 | 7/2010 | Steed et al. |
| 2011/0191343 A1 | 8/2011 | Heaton et al. |
| 2011/0025059 A1 | 10/2011 | Larson et al. |
| 2011/0252353 A1 | 10/2011 | Janaway et al. |
| 2012/0078601 A1 | 3/2012 | Avinash et al. |
| 2015/0269756 A1 | 9/2015 | Leong et al. |
| 2018/0225415 A1 | 8/2018 | Majumdar |

OTHER PUBLICATIONS

Milbury et al. Determining lower limits of detection of digital PCR assays for cancer-related gene mutations. 2014 Biomolecular Detection and Quantification vol. 1 p. 8-22. 2014. (Year: 2014).*

Dreo et al. Optimizing droplet digital PCR analysis approaches for detection and quantification of bacteria: a case study of fire blight and potato brown rot. Analytical Bioanalytical Chemistry 2014 vol. 406 p. 6513-6528. (Year: 2014).*

International Preliminary Report on Patentability and Written Opinion issued in Application No. PCT/US2016/035870, dated Dec. 5, 2017.

Raul Rojas, "The Secret Life of the Covariance Matrix", Jan. 31, 2009, Retrieved from the Internet: URL:http://www.inf.fu-berlin.de/inst/ag-ki/rojas_home/documents/tutorials/secretcovariance.pdf.

Coren A. Milbury et al., "Determining lower limits of detection of digital PCR assays for cancer-related gene mutations", Biomolecular Detection and Quantification, vol. 1, No. 1, Sep. 1, 2014, pp. 8-22.

International Preliminary Report on Patentability and Written Opinion issued in International Application No. PCT/US2016/042553 dated Jan. 23, 2018.

Digital PCR Analysis Software version 3, Aug. 6, 2010; Surface modification in microchip electrophoresis, 2003.

Chinese Supplementary Search Report issued in Chinese Application No. 2013800694247, dated Jul. 15, 2019.

European Communication issued in Application No. 13 799 705.2, dated Jan. 31, 2019.

DPlot Graph Software for Scientists and Engineer, Oct. 7, 2011.

"Applied Biosystems StepOne and StepOnePlus Real-Time PCR Systems for Genotyping Experiments", Getting Started Guide, Jun. 2010, 1-156.

"Digital PCR Analysis Software version 3", Fluidigm User Guide, 2011, 1-91.

International Preliminary Report on Patentability and Written Opinion for Application No. PCT/US2013/068984, dated May 12, 2015, 14 pages.

International Search Report and Written Opinion of the ISA for Int'l Application No. PCT/US2013/068984, dated Jun. 12, 2014.

Whale, Alexandra S. et al., "Comparison of Microfluidic Digital PCR and Conventional Quantitative PCR for Measuring Copy Number Variation", Nucleic Acids Research, vol. 40, No. 11, e82, Feb. 2012, 1-9.

Zhong, Qun et al., "Multiplex Digital PCR: breaking the one target per color barrier of quantitative PCR", Lab on a Chip, vol. 11, 2011, 2167-2174.

* cited by examiner

DETERMINING THE LIMIT OF DETECTION OF RARE TARGETS USING DIGITAL PCR

BACKGROUND

Detection and quantification of mutant alleles in tumor tissue is important to cancer research. Testing for the presence of mutations in circulating free DNA (cfDNA) is one of the less invasive research methods available at this time. Digital PCR presents a research tool for mutation detection in cfDNA at a sensitivity level of 1% and below.

The digital method segments sample DNA into a large number of reaction partitions. Upon performing PCR, amplification is detected in reactions with DNA template and no amplification is detected in reactions lacking DNA template. This large scale partitioning isolates the rare target within a subset of partitions, elevates the rare to wild-type ratio within any specific partition (compared to the original PCR mix), and enhances the amplification probability and detectability of the rare target. These three effects enable detection of the rare target with high sensitivity.

Challenges associated with digital PCR experiments for rare allele detection include understanding the limit of detection of the assay and platform. Data points corresponding to rare target are by definition far fewer than the data points corresponding to positives for the wild-type target. This makes identification of the rare target challenging. One known approach to addressing this challenge requires overlaying wild-type control data with positive control data to guide the definition for a boundary of the wild-type event in fluorescence space. The data points outside of this boundary are considered true positives for the rare target for unknown sample (and false positives for a control sample with wild-type only target). This strategy only works when the inter-run variation in signal levels is negligible and/or when a specific normalization is applied to account for such variation.

A need therefore exists for a more robust approach that works independent of interrun variations in signal levels.

SUMMARY

In one exemplary embodiment, a method for determining false positives calls in a biological data plot is provided. The method includes identifying a first data cluster as non-amplification data points within the biological data plot and identifying a second data cluster as wild-type positives within the biological data plot. The method further includes estimating a position in the biological data plot of a center of the first and second data clusters. The method further includes determining, for each data point within the first data cluster, a probability of belonging to the first data cluster and determining, for each data point within the second data cluster, a probability of belonging to the second data cluster. The method includes applying a probability threshold for each data point within the first and second data cluster to identify false positives.

DETAILED DESCRIPTION

Figure 1A:
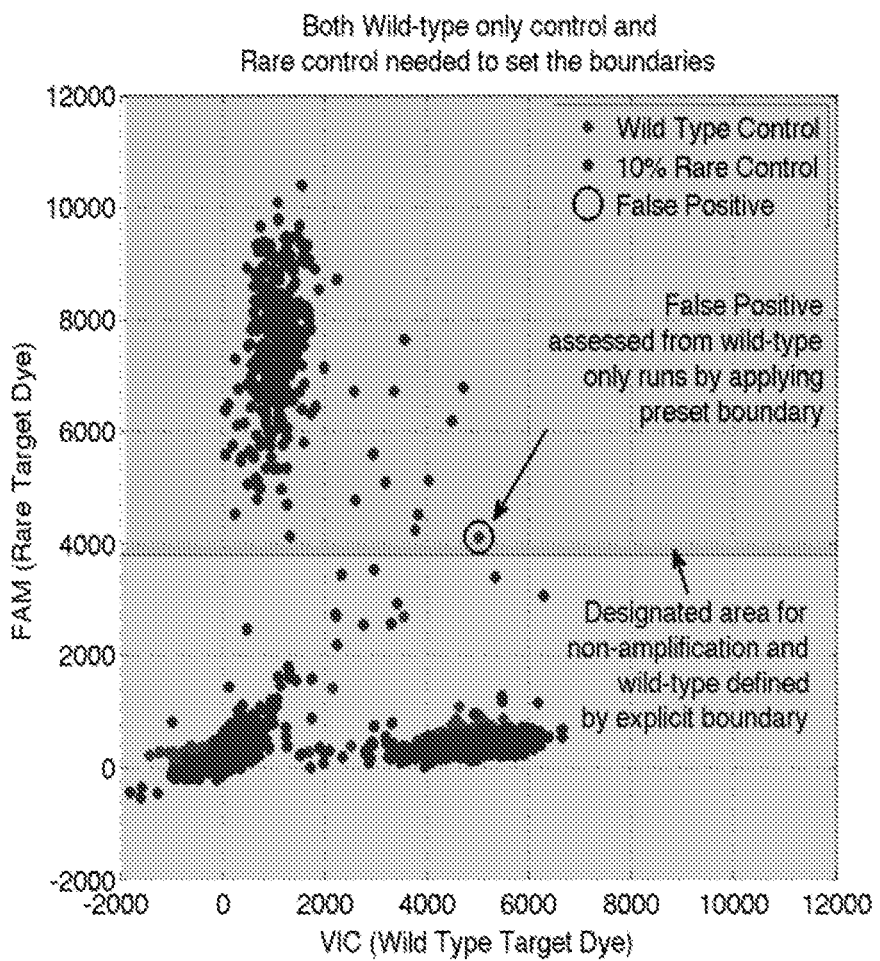
FIG. 1A illustrates a known method (Method A) identifying false positive events when in the detection of rare targets according to various embodiments described herein.

Data points corresponding to rare target are by definition far fewer than the data points corresponding to positives for the wild-type target. This makes identification of the rare target challenging. A known method (method A) for solving this challenge is described below.

Known Method A

The data from the wild-type control is overlaid with the data from the positive control to guide the definition for a boundary of the wild-type event in fluorescence space. The data points outside of this boundary are considered true positives for the rare target for unknown sample (and false positives for a control sample with wild-type only target). This strategy works when the inter-run variation in signal levels is negligible or when a specific normalization is applied to account for such variation.

A more reliable method (Method B), according to various embodiments, for solving this challenge is described below:

Method B

A second approach, described in the present disclosure, identifies the center of the non-amplification cluster and of the wild-type positive cluster. This approach next evaluates, for each data point, the probabilities $\{p1,p2\}$ of belonging to either of these clusters. The final step establishes, again for each data point, a single probability, $p=\max\{p1, p2\}$), upon which a threshold may be applied to identify outlier events that do not belong within one of these main clusters. This strategy is more robust as it works independent of interrun variations in signal levels. It is based on the assumption of finding a sizable non-amplification and wildtype positive clusters.

If false positives are identified using control chips, lower limits on detectable concentration of the rare target can be established. Replicate runs may be used to get an understanding of the distribution of false positive events for a given assay system. Then, a lower limit of detection (above the false positive rate) of the assay system can be calculated.

The present disclosure relates, in some embodiments, to a method for identifying false positive events in the detection of rare targets. The method can include identifying the center of the non-amplification cluster and of the wild-type positive cluster. This method can also include evaluating, for each data point, the probabilities (e.g., $\{p1,p2\}$) of belonging to either of the identified clusters. This method can further include establishing, for each data point, a single probability (e.g., $p=\max\{p1, p2\}$) upon which a threshold may be applied to identify outlier events that do not belong within one of these main clusters.

This method is more robust than known approaches to false positive assessment strategies as it works independent of interrun variations in signal levels. It is based, among other things, on an assumption of finding a sizable non-amplification and wild-type positive clusters.

If false positives are identified using control chips, lower limits on detectable concentration of the rare target can be established. Replicate runs may be used to get an understanding of the distribution of false positive events for a given assay system. Then, a lower limit of detection (above the false positive rate) of the assay system can be calculated.

This description below compares a known false positive assessment method to a method of the present disclosure, using the signal levels of the no-amplification cluster and the wild-type cluster where available. Once the false positive call rate is established, this description below outlines a method to determine the limit of detection of the assay and platform, at a given level of confidence. Given the number of partitions, the interrogated volume and the false call rate, the tradeoffs between sample load and sensitivity are also discussed.

The mathematics outlined to calculate the theoretical limit of detection is applied on a set of assays covering the KRAS codon mutations commonly found in tumor tissues. Experimental results showing a detection of at least 0.1% mutation rate are presented as examples. Test samples were created using both mutant plasmid and mutant genomic DNA mixed with wild-type genomic DNA at a predefined percentage.

Experimental Design Considerations

While the false positive rate puts a lower limit on the concentration of rare targets that can be reliably measured, there are two other considerations for sensitivity: 1) The larger the interrogated volume, the higher the sensitivity (or the lower the concentration that you can detect); and 2) The minimum in-partition rare to wild-type ratio that can be tolerated by the assay dictates how much wild-type target may be loaded on to the chip.

Experimental Protocol

Materials: 0.1×TE Buffer from 1×TE Buffer, 6.8 ng/uL gDNA from 100 ng/uL or 10 ng/uL gDNA, "1×" plasmid from "10×" plasmid, sample plate (e.g., QuantStudio™ 3D Chips), a PCR thermal cycler, and a fluorescence detection or reader instrument (e.g., QuantStudio™ 3D instrument).

Mixture Creation: Prep loading mixture for "10%" chips: In a labeled tube (1.5 mL or 0.5 mL), pipet in the following: 40 µL of Master Mix, 20 µL of 6.8 ng/p1 gDNA, 16 uL of "10×" plasmid, 4 µL of the 20× rare mutation assay. Vortex the finished tube. For 1% chips, dilute the plasmid to a "1×" tube and use 16 µL of the "1×". For wild type chips, replace the 16 µL of plasmid with 16 µL of ultrapure water.

Run: Load 14.5 µL on each sample plate (e.g., QuantStudio™ 3D chip) and thermal cycle per the rare mutation assay thermal cycling conditions prior to imaging on the fluorescence detection or reader instrument (e.g., QuantStudio™ 3 D instrument), following the protocol prescribed for rare mutation assays.

Analysis Protocol: False Positive Identification

Figure 1B:
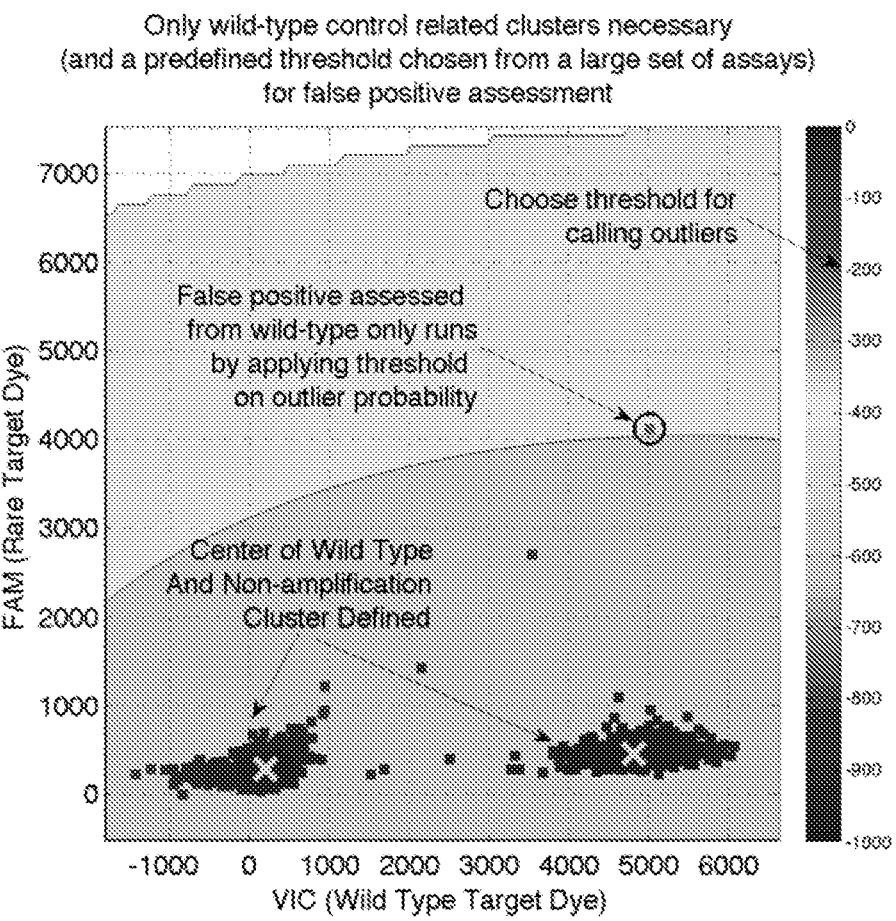
FIG. 1B illustrates a method of the present disclosure (Method B) for identifying false positive events when in the detection of rare targets according to various embodiments described herein.

FIG. 1A and FIG. 1B shows two methods for identifying false positives from non-template controls and wild-type control runs. FIG. 1A illustrates a known method (Method A) of designating the non-amplification and wild-type positive cluster area in fluorescence space by explicit boundary, and designating points outside of this area designated as false positives. FIG. 1B illustrates a method of the present disclosure for identifying false positives, the method including estimating cluster centers and spread respectively from the non-amplification and wild-type positives, fitting to a two dimensional Gaussian model, and applying a threshold on log probability for belonging to modeled cluster to identify false positives.

As discussed above, it is a challenge to draw boundaries where the density of points is low, trying to decide whether or not a point on the edge of a cluster is a real positive or not, as necessary to apply Method A. This method only works when the inter-run variation in signal levels is negligible and/or when a specific normalization is applied to account for such variation. On the other hand, Method B can require identification of centers of clusters that have significant membership.

Equation set 1 below describes the model used to calculate the likelihood of outlier status for a given data point, when both the non-amplification cluster and the wild-type positive cluster exists (wild-type control). This can easily be generalized to the case where only the non-amplification cluster exists (non-template control).

Let the probabilities p1 and p2 denote the probability of belonging with the non-amplification and the wild type positive cluster respectively.

$$p_1(v, f) = C \times \exp\left[-\frac{1}{2} A \sum_A^{-1} A^T\right]$$

$$p_2(v, f) = C \times \exp\left[-\frac{1}{2} B \sum_B^{-1} B^T\right]$$

where:
C is the constant associated with the 2D Gaussian modeling (Here, C=1)

$$A = \begin{pmatrix} v - \mu_v \\ f - \mu_f \end{pmatrix}$$

with means calculated from the non-amplification cluster $$B = \begin{pmatrix} v - \mu_v \\ f - \mu_f \end{pmatrix}$$

with means calculated from the wild-type positive cluster
Σ is the covariance matrix $$\begin{pmatrix} \text{var}(f) & \text{cov}(f, v) \\ \text{cov}(f, v) & \text{var}(f) \end{pmatrix}$$

with $\Sigma_A$ calculated from the non-amplification cluster and $\Sigma_B$ calculated from the wild-type positive cluster respectively.

$$p(v,f) = \max(p1, p2)$$

A set of 42 TaqMan® assays were chosen with 4 replicate runs of the wild-type control. Positive controls at 1 to 10% titration of the mutant alleles to fixed concentration of the wild-type allele were also run for these assays. Based upon this data, a threshold of −200 on log(p) is chosen to identify a true false positive distinct from the scatter at the periphery of the wildtype cluster. A true false positive is a positive on a control that would cluster with true rare target positives).

Apart from signal strength (method A), and separation from main clusters (method B), one last factor to consider for false positive determination is the through-hole level quality value of the specific point and its neighboring points, if working with an array based technology where this information is available, such as the QuantStudio 3D platform. Using high quality data points (or points from a high data quality region) is recommended.

Analysis Protocol: Estimating the False Positive Rate and the Limit of Detection Once the number of false positives for the $i^{th}$ run is available, it is normalized by the wild-type load per equation 2 (from Coren A. Milbury, Qun Zhong, Jesse Lin, Miguel Williams, Jeff Olson, Darren R. Link, Brian Hutchison. "Determining the lower limits of detection of digital PCR assays for cancer-related gene mutations." Biomolecular Detection and Quantification. Volume 1, Issue 1. September 2014, Pages 8-22) (hereinafter "Milbury").

$$\text{Normalized \#False Positive } i = \left( \frac{1}{k} \sum_{run\# j=1}^{k} \frac{\gamma_{mutant}^j}{\gamma_{wild-type}^j} \right) \times \gamma_{wild-type}^i \times N_i$$

And then the lowest limit of detection for that assay system is determined per equation set 3 (see, Milbury).

| $\Lambda_{FP}$ | LoB | LoD |
|---|---|---|
| 0 | 0 | 3 |
| 0-0.5 | 1 | 5 |
| >0.05 | $\Lambda_{FP} + 1.645 \sqrt{\Lambda_{FP}} + .8$ | $(1.645 + \sqrt{1.645^2 + 4 LoB^2})/4$ | where $\Lambda_{FP}$ is the normalized average number of false positives per run, LoB is the limit of blank and LoD is the limit of detection.

Note that knowing the average number of false positives does not allow us to correct an answer when evaluating unknown targets. At a given run, the actual number of false positives can take any value. Therefore the best use of the false positive rate knowledge is for determining what the minimum number of events above which we can reliably conclude that the observed set of data is different from the false positive distribution.

Results

Ten runs from KRAS 516 are annotated by manual calling. Method B is then deployed to estimate the rare dye. The estimated number is compared to the annotation result and shows good correspondence (Table 1).

Figure 2A:
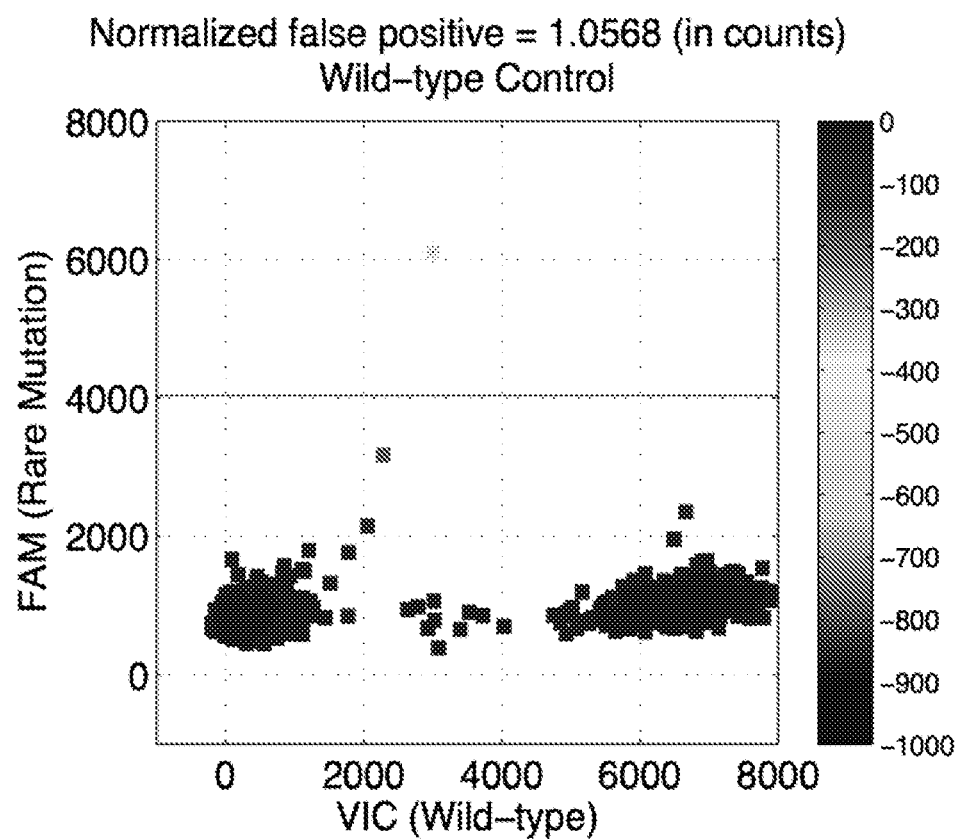
FIGS. 2A-2B illustrate duplicate runs at 0% target to total ratio (control) according to various embodiments described herein.
Figure 2B:
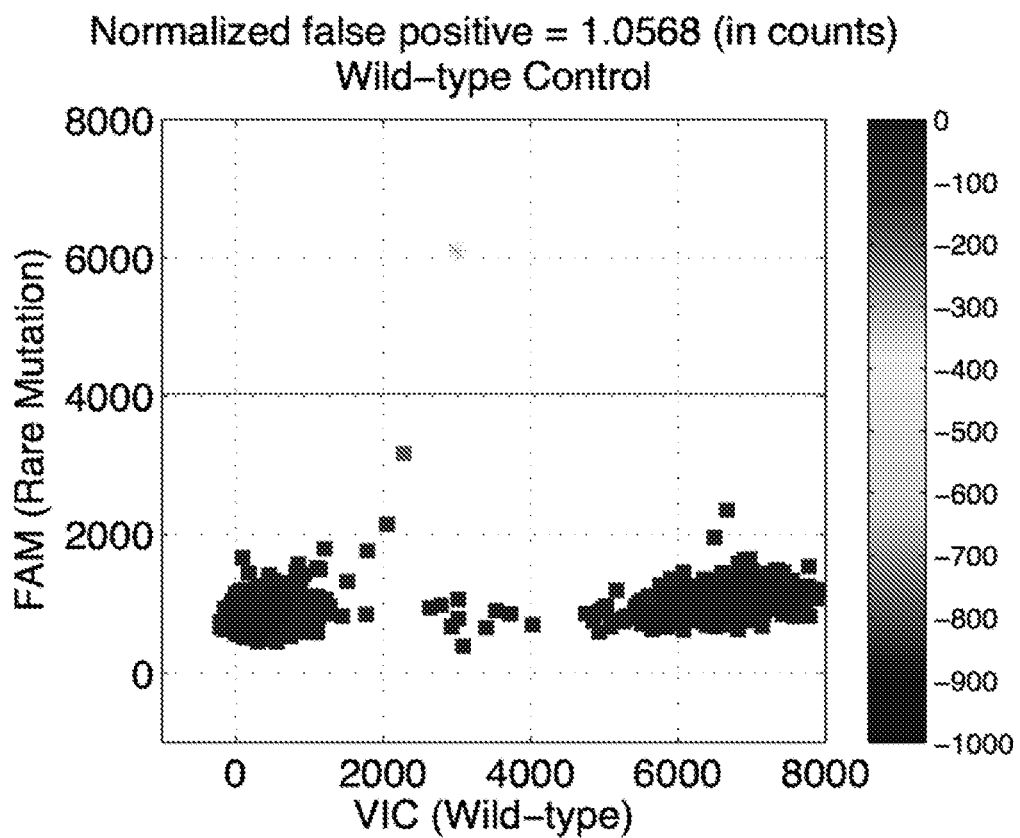
Figure 3A:
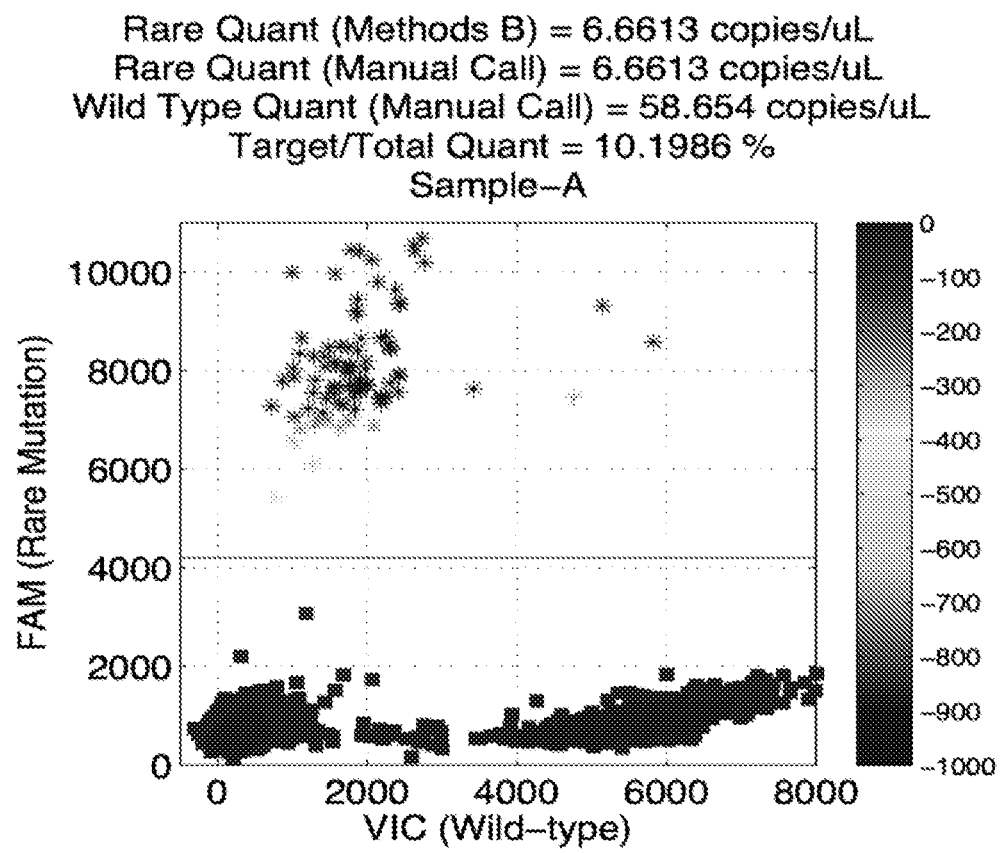
FIGS. 3A-3B illustrate duplicate runs at 10% target to total ratio according to various embodiments described herein.
Figure 3B:
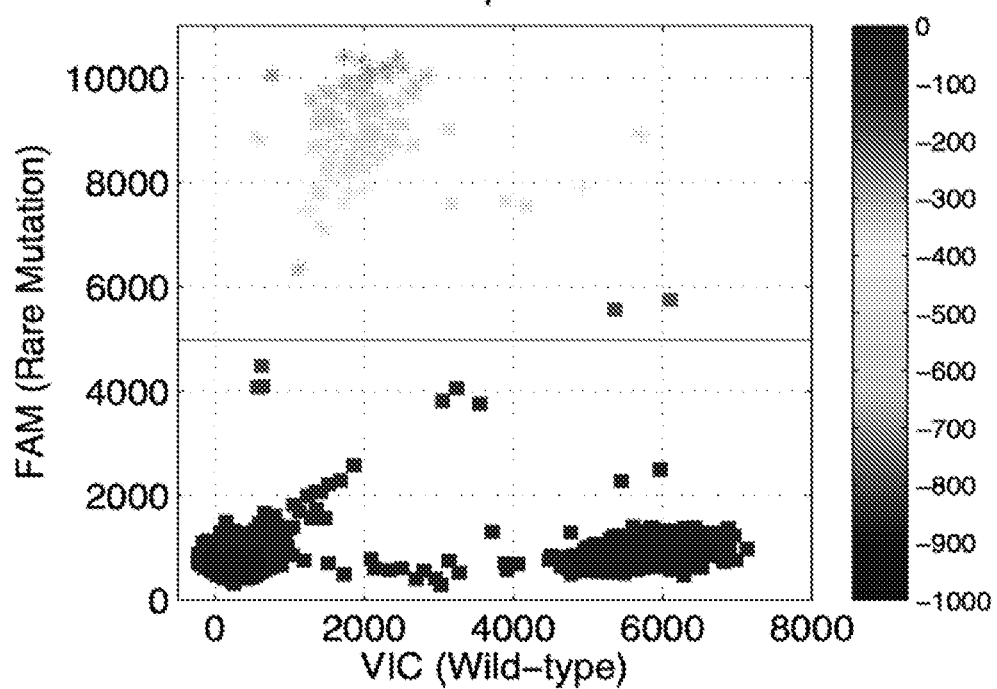
Figure 4A:
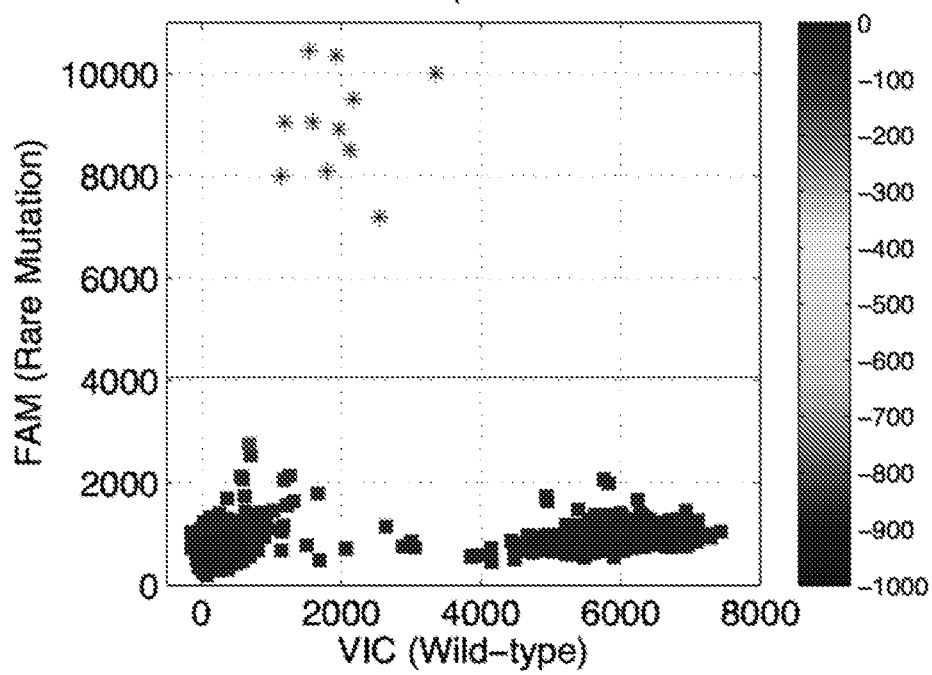
FIGS. 4A-4B illustrate duplicate runs at 1% target to total ratio according to various embodiments described herein.
Figure 4B:
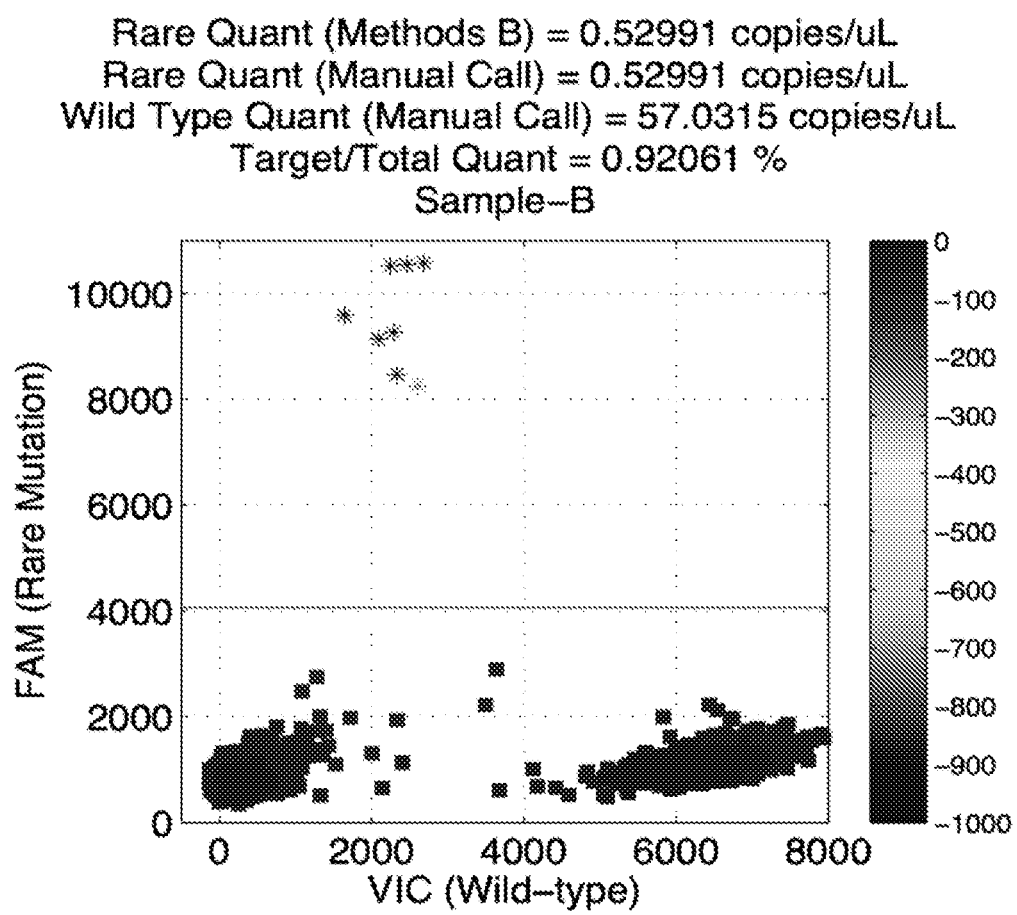
Figure 5A:
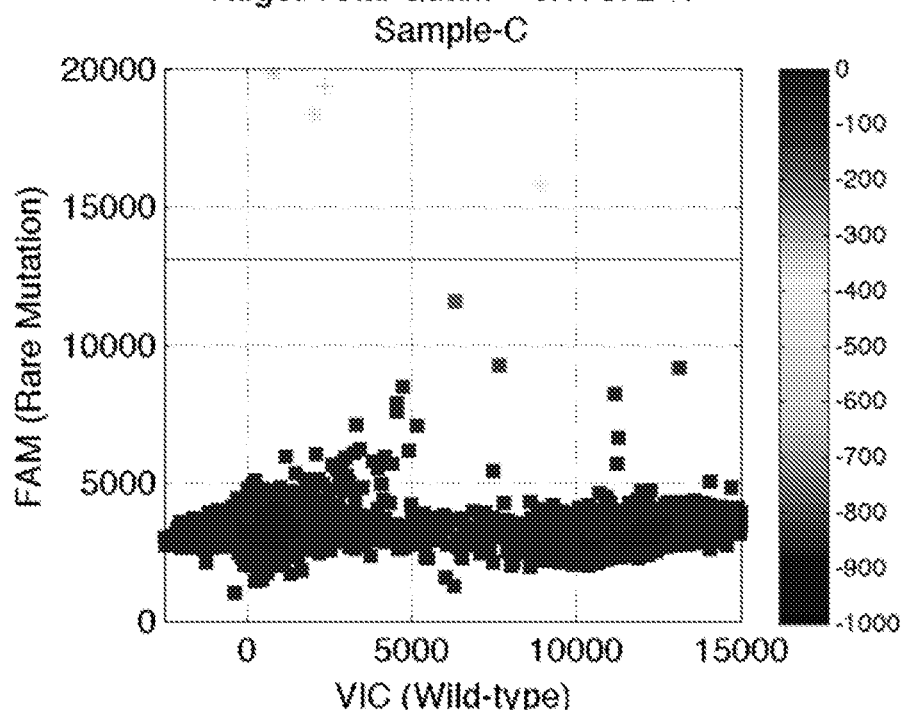
FIGS. 5A-5B illustrate duplicate runs at 0.1% target to total ratio according to various embodiments described herein.
Figure 5B:
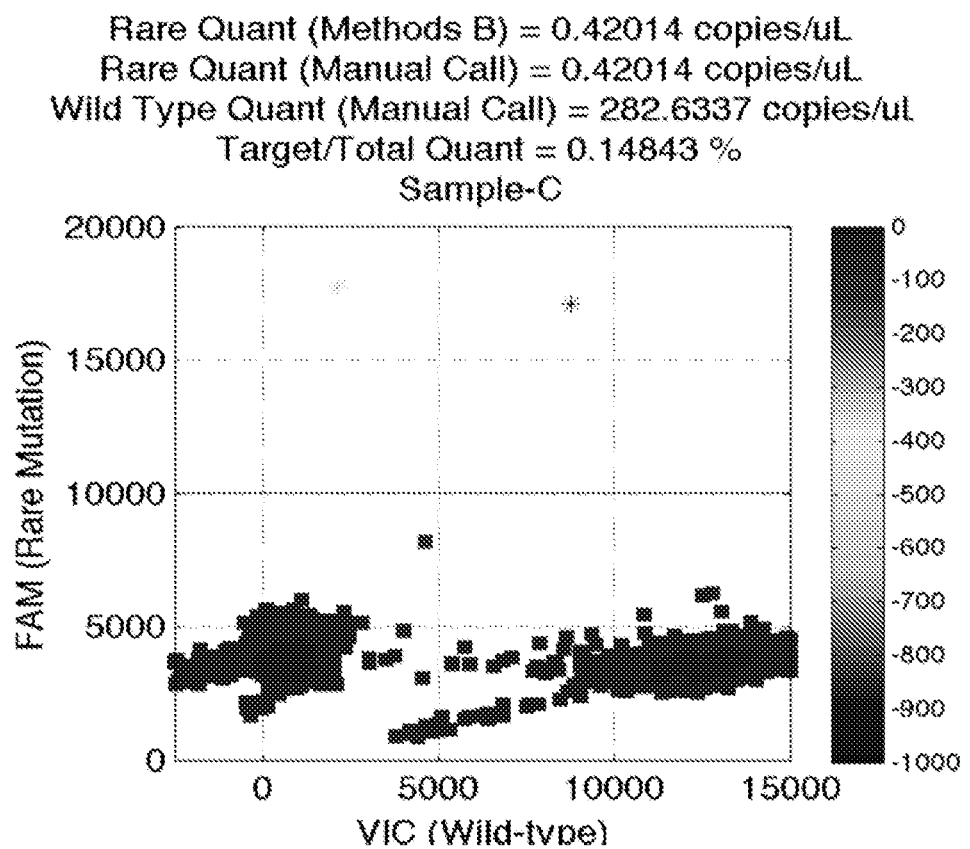

Wild-type only control, and rare mutation at set proportions to the wild type were run for assays targeting the KRAS 521 in duplicates. In particular, similar experiments were run for KRAS 521 in duplicates at 0% (Wild-type only control), 0.1%, 1%, and 10% target to total ratios. Provided in FIGS. 2-5 are data from each run and the quantifications based upon manual calling compared to method B. Again, we see good agreement. In particular, FIGS. 2A-2B illustrate duplicate runs at 0% target to total ratio (control), FIGS. 3A-3B illustrate duplicate runs at 10% target to total ratio, FIGS. 4A-4B illustrate duplicate runs at 1% target to total ratio, and FIGS. 5A-5B illustrate duplicate runs at 0.1% target to total ratio. In each FIG., rare target quantification by manual setting of threshold, indicated by the lines (Method A), match well with those predicted by Method B (indicated by * symbol) yielding up to 0.1% rare mutation detection.

As detailed in the foregoing, one can evaluate a signal level above which a data point will be considered as a positive, typically done using both positive and wild-type controls as described in Method A. This is susceptible to run to run variation in signal levels. This disclosure introduces an alternate method based upon the assumption that there is sufficient numbers of points belonging to the non-amplification cluster and the positive cluster for the wild-type target (unless the run is a no template control, in which case you only have the non-amplification cluster). The statistics of these one or two dominant clusters are used to assess if a given point belongs with these cluster or not. If not, they are suitable to be labeled as outliers or false positives, as described by Method B. The efficacy of this method is demonstrated by the predicting of the rare concentration correctly where the true rare data points have been manually annotated. Once the number of false positives are determined, they are normalized across replicates by known methods (see, for example, those recommended in Milbury), and based upon the normalized rate, the lowest limit of detection is also evaluated as described in, for example, Milbury.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited

TABLE 1

Results using a candidate assay design targeting KRAS 516

| Chip # | Task | Wild Type Copies/μL | # Mutant (annotated) | Mutant Copies/μL (annotated) | # Mutant (Method B) | Mutant Copies/μL (Method B) | Normalized Number of False Positive |
|---|---|---|---|---|---|---|---|
| 1 | Unknown | 51.75 | 325 | 20.47 | 324 | 20.41 | |
| 2 | Unknown | 64.11 | 308 | 20.48 | 295 | 19.68 | |
| 3 | Unknown | 65.15 | 333 | 22.92 | 331 | 22.79 | |
| 4 | Unknown | 61.11 | 30 | 1.98 | 31 | 2.04 | |
| 5 | Unknown | 54.67 | 39 | 2.69 | 41 | 2.83 | |
| 6 | Unknown | 59.85 | 34 | 2.28 | 34 | 2.28 | |
| 7 | Wild-type | 50.81 | 1 | 0.06 | 10 | 0 | 1.54 |
| 8 | Wild-type | 59.54 | 2 | 0.16 | 1 | 0.08 | 1.45 |
| 9 | Wild-type | 51.05 | 1 | 0.07 | 1 | 0.07 | 1.50 |
| 10 | Wild-type | 58.83 | 2 | 0.15 | 2 | 0.15 | 1.52 |
| | Average False Positive Rate from Wild-type Runs | | | | | | 1.51 |
| | Lowest Limit of Detection at 95% Confidence | | | | | | 3.85 | functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the present teachings.

Figure 6:
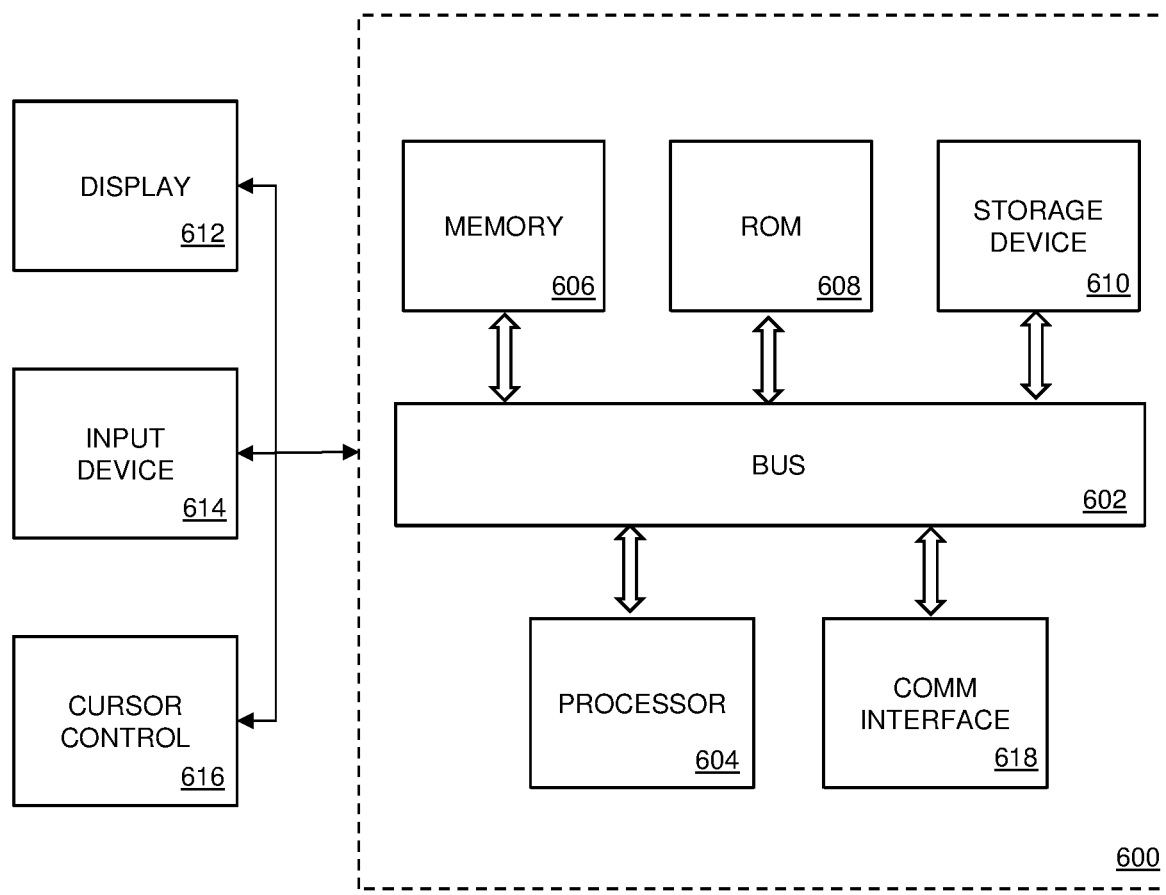
FIG. 6 illustrates an exemplary computing system for implementing various embodiments described herein.

FIG. 6 is a block diagram that illustrates a computer system 600 that can be employed to carry out processing functionality, and to implement various components or subsystems of the systems described herein according to various embodiments. For example, system 600 can comprise all or apportion of devices 540, client devices, 502, 512, or 530, servers 522, etc. Computing system 600 can include one or more processors, such as a processor 604. Processor 604 can be implemented using a general or special purpose processing engine such as, for example, a microprocessor, controller or other control logic. In this example, processor 604 is connected to a bus 602 or other communication medium.

Further, it should be appreciated that a computing system 600 of FIG. 6 can be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 600 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 600 may be configured to connect to one or more servers in a distributed network. Computing system 600 may receive information or updates from the distributed network. Computing system 600 may also transmit information to be stored within the distributed network that may be accessed by other clients connected to the distributed network.

Computing system 600 may include bus 602 or other communication mechanism for communicating information, and processor 604 coupled with bus 602 for processing information.

Computing system 600 also includes a memory 606, which can be a random access memory (RAM) or other dynamic memory, coupled to bus 602 for storing instructions to be executed by processor 604. Memory 606 also may be used for storing temporary variables or other intermediate information during execution of instructions to be executed by processor 604. Computing system 600 further includes a read only memory (ROM) 608 or other static storage device coupled to bus 602 for storing static information and instructions for processor 604.

Computing system 600 may also include a storage device 610, such as a magnetic disk, optical disk, or solid state drive (SSD) is provided and coupled to bus 602 for storing information and instructions. Storage device 610 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 610 may include other similar instrumentalities for allowing computer programs or other instructions or data to be loaded into computing system 600. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 610 to computing system 600.

Computing system 600 can also include a communications interface 618. Communications interface 618 can be used to allow software and data to be transferred between computing system 600 and external devices. Examples of communications interface 618 can include a modem, a network interface (such as an Ethernet or other NIC card), a communications port (such as for example, a USB port, a RS-232C serial port), a PCMCIA slot and card, Bluetooth, etc. Software and data transferred via communications interface 618 are in the form of signals which can be electronic, electromagnetic, and optical or other signals capable of being received by communications interface 618. These signals may be transmitted and received by communications interface 618 via a channel such as a wireless medium, wire or cable, fiber optics, or other communications medium. Some examples of a channel include a phone line, a cellular phone link, an RF link, a network interface, a local or wide area network, and other communications channels.

Computing system 600 may be coupled via bus 602 to a display 612, such as a cathode ray tube (CRT) or liquid crystal display (LCD), for displaying information to a computer user. An input device 614, including alphanumeric and other keys, is coupled to bus 602 for communicating information and command selections to processor 604, for example. An input device may also be a display, such as an LCD display, configured with touchscreen input capabilities. Another type of user input device is cursor control 616, such as a mouse, a trackball or cursor direction keys for communicating direction information and command selections to processor 604 and for controlling cursor movement on display 612. This input device typically has two degrees of freedom in two axes, a first axis (e.g., x) and a second axis (e.g., y), that allows the device to specify positions in a plane. A computing system 600 provides data processing and provides a level of confidence for such data. Consistent with certain implementations of embodiments of the present teachings, data processing and confidence values are provided by computing system 600 in response to processor 604 executing one or more sequences of one or more instructions contained in memory 606. Such instructions may be read into memory 606 from another computer-readable medium, such as storage device 610. Execution of the sequences of instructions contained in memory 606 causes processor 604 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 604 for execution.

Such instructions, generally referred to as "computer program code" (which may be grouped in the form of computer programs or other groupings), when executed, enable the computing system 600 to perform features or functions of embodiments of the present embodiments described herein. These and other forms of non-transitory computer-readable media may take many forms, including but not limited to, non-volatile media, volatile media, and transmission media. Non-volatile media includes, for example, solid state, optical or magnetic disks, such as storage device 610. Volatile media includes dynamic memory, such as memory 606. Transmission media includes coaxial cables, copper wire, and fiber optics, including the wires that comprise bus 602.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 604 for execution. For example, the instructions may initially be carried on magnetic disk of a remote computer. The remote computer can load the instructions into its dynamic memory and send the instructions over a telephone line using a modem. A modem local to computing system 600 can receive the data on the telephone line and use an infra-red transmitter to convert the data to an infra-red signal. An infra-red detector coupled to bus 602 can receive the data carried in the infra-red signal and place the data on bus 602. Bus 602 carries the data to memory 606, from which processor 604 retrieves and executes the instructions. The instructions received by memory 606 may optionally be stored on storage device 610 either before or after execution by processor 604.

It will be appreciated that, for clarity purposes, the above description has described embodiments with reference to different functional units and processors. However, it will be apparent that any suitable distribution of functionality between different functional units, processors or domains may be used without detracting from the embodiments of the present teachings. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Figure 7:
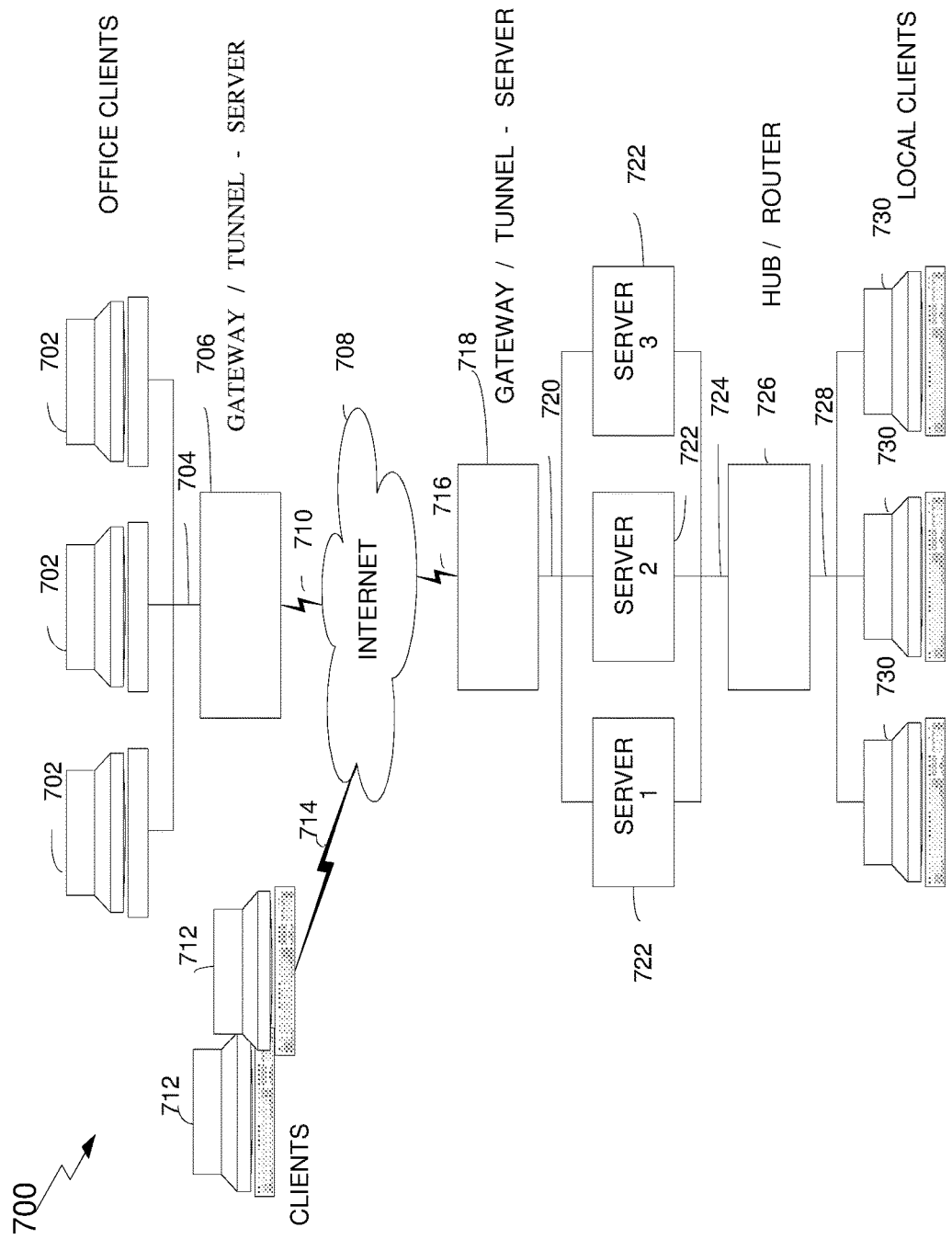
FIG. 7 illustrates an exemplary distributed network system according to various embodiments described herein.

FIG. 7 is a diagram illustrating an example system 700 configured in accordance with one example embodiment. In system 700, one or more servers 722 can be configured to run the analysis applications for analyzing data sets produced by one or more devices or modalities 740. The data included in the data sets can be stored in one or more storage devices 750. Once the data sets have been uploaded to servers 722, then a plurality of applications running on servers 722 can be used to manipulate, analyze and visualize the data sets from anywhere. For example, local client devices 730 can be used to access servers 722, e.g., through a hub or router 726. At the same time, the data can be accessed remotely through remote clients devices 702, which are interfaced with servers 722, e.g., via a gateway/hub/tunnel-server/etc. 710, which is itself connected to the internet 708 via some internet service provider (ISP) connection 710, or remote client servers 712, which are interfaced with servers 722, e.g., via the internet 708 and via an ISP connection 714.

It should also be noted that devices 740 can be directly interfaced with servers 722, e.g., through the internet. In such embodiments, the collection application and functionality can reside on servers 722, on devices 740, or both. In other embodiments, devices 740 can be interfaced with client devices 702 or 712. In such embodiments, the collection application or functionality can be included on client devices 702 or 712, devices 740, or both.

Client devices 702, 712, and 730 can be any kind of computing device that can be used to access servers 722. As such, these devices can be laptop, desktop, or palmtop computers, terminals, mobile computing devices such as smartphones or tablets, etc. Servers 722 can comprise one or more processors, servers, routers, co-processors, user interfaces, etc., whether co-located or located in different locations. In short, servers 722 can comprise all of the resources, both hardware and software, needed to perform the functions described herein. A more detailed description of a computer system and the resources that can be used to implement the components illustrated in FIG. 7 is described below with respect to FIG. 6.

Although various embodiments have been described with respect to certain exemplary embodiments, examples, and applications, it will be apparent to those skilled in the art that various modifications and changes may be made without departing from the present teachings.

What is claimed is:

1. A method for establishing a limit of detection for a biological analysis system configured to detect rare target nucleic acid, the method comprising:

generating, using one or more processors, a cluster plot of data points, wherein:
axes of the cluster plot correspond to first fluorescence intensity corresponding to a first fluorescence dye and second fluorescence intensity corresponding to a second fluorescence dye, respectively, and
the cluster plot of data points comprises data obtained from fluorescence emission, detected by an analytical instrument of the biological analysis system, from a plurality of reaction volumes partitioned from a control biological sample and subjected to a first polymerase chain reaction (PCR) assay using the first fluorescence dye as a label, the control biological sample containing wild-type template nucleic acid and the first PCR assay being configured to amplify the wild-type template nucleic acid;

identifying, using the one or more processors, a first cluster of data points of the cluster plot as non-amplification data points, the non-amplification data points corresponding to a first set of the plurality of reaction volumes from which no amplification product of the wild-type template nucleic acid was detected based on the fluorescence emission detected;

identifying, using the one or more processors, a second cluster of data points as wild-type data points, the wild-type data points corresponding to a second set of the plurality of reaction volumes in which amplified product of the wild-type template nucleic acid was detected based on the fluorescence emission detected;

estimating, using the one or more processors, a first coordinate of the cluster plot of data points as a center of the first cluster of data points and a second coordinate of the cluster plot as a center of the second cluster of data points;

determining, using the one or more processors, for each data point of the cluster plot, a first probability of belonging to the first cluster of data points based on a distance of the data point from the first coordinate;

determining, using the one or more processors, for each data point of the cluster plot, a second probability of belonging to the second cluster of data points based on a distance of the data point from the second coordinate;

determining, using the one or more processors, for each data point of the cluster plot, a third probability of belonging to either of the first cluster of data points or the second cluster of data points based on the first probability and the second probability;

comparing, using the one or more processors, the third probability for each data point of the cluster plot to a probability threshold;

based on the comparing, identifying, using the one or more processors, one or more data points of the cluster plot of data points, as one or more false positive data points not belonging to either the first cluster of data points or the second cluster of data points;

establishing, using the one or more processors, a limit of detection for the biological analysis system configured to detect rare target nucleic acid based on information from identifying the one or more false positive data points; and identifying, using the one or more processors, rare target nucleic acid in a test biological sample based on data points obtained from fluorescence emission, detected by the analytical instrument, from a plurality of reaction volumes partitioned from the test biological sample and subjected to a second PCR assay configured to amplify the rare target nucleic acid, wherein the second PCR assay uses the second fluorescence dye as a label for the detecting, and wherein the data points exceed the established limit of detection.

2. The method of claim 1, further comprising determining, using the one or more processors, a measure of spread between the estimated first and second coordinates of the centers of the first and second clusters of data points, wherein determining the third probability is further based on the measure of spread.

3. A computer-readable storage medium comprising instructions, executable by one or more processors, for establishing a limit of detection for a biological analysis system configured to detect rare target nucleic acid, the instructions comprising instructions for:

generating a cluster plot of data points, wherein:
axes of the cluster plot correspond to first fluorescence intensity corresponding to a first fluorescence dye and second fluorescence intensity corresponding to a second fluorescence dye, respectively, and the cluster plot of data points comprises data obtained from fluorescence emission, detected by an analytical instrument of the biological analysis system, from a plurality of reaction volumes partitioned from a control biological sample and subjected to a first polymerase chain reaction (PCR) assay using the first fluorescence dye as a label, the control biological sample containing wild-type template nucleic acid and the first PCR assay being configured to amplify the wild-type template nucleic acid;

identifying a first cluster of data points of the cluster plot as non-amplification data points, the non-amplification data points corresponding to a first set of the plurality of reaction volumes from which no amplification product of the wild-type template nucleic acid was detected based on the fluorescence emission detected;

identifying a second cluster of data points as wild-type data points, the wild-type data points corresponding to a second set of the plurality of reaction volumes in which amplified product of the wild-type template nucleic acid was detected based on the fluorescence emission detected;

estimating a first coordinate of the cluster plot of data points as a center of the first cluster of data points and a second coordinate of the cluster plot as a center of the second cluster of data points;

determining, for each data point of the cluster plot, a first probability of belonging to the first cluster of data points based on a distance of the data point from the first coordinate;

determining, for each data point of the cluster plot, a second probability of belonging to the second cluster of data points based on a distance of the data point from the second coordinate;

determining for each data point of the cluster plot, a third probability of belonging to either of the first cluster of data points or the second cluster of data points based on the first probability and the second probability;

comparing the third probability for each data point of the cluster plot to a probability threshold;

based on the comparing, identifying one or more data points of the cluster plot of data points, as one or more false positive data points not belonging to either the first cluster of data points or the second cluster of data points;

establishing a limit of detection for the biological analysis system configured to detect rare target nucleic acid based on information from identifying the one or more false positive data points; and identifying, using the one or more processors, rare target nucleic acid in a test biological sample based on data points obtained from fluorescence emission, detected by the analytical instrument, from a plurality of reaction volumes partitioned from the test biological sample and subjected to a second PCR assay configured to amplify the rare target nucleic acid, wherein the second PCR assay uses the second fluorescence dye as a label for the detecting, and wherein the data points exceed the established limit of detection.

4. The computer-readable storage medium of claim 3, wherein the instructions further comprise instructions for determining a measure of spread between the estimated first and second coordinates of the centers of the first and second clusters of data points, wherein determining the third probability is further based on the determined spread.

5. A biological analysis system, the system comprising:
one or more processors; and
a memory comprising instructions, executable by the one or more processors, for:
generating, using one or more processors, a cluster plot of data points, wherein:
axes of the cluster plot correspond to first fluorescence intensity corresponding to a first fluorescence dye and second fluorescence intensity corresponding to a second fluorescence dye, respectively, and
the cluster plot of data points comprises data obtained from fluorescence emission, detected by an analytical instrument, from a plurality of reaction volumes partitioned from a control biological sample and subjected to a first polymerase chain reaction (PCR) assay using the first fluorescence dye as a label, the control biological sample containing wild-type template nucleic acid and the first PCR assay being configured to amplify the wild-type template nucleic acid;

identifying, using the one or more processors, a first cluster of data points of the cluster plot as non-amplification data points, the non-amplification data points corresponding to a first set of the plurality of reaction volumes from which no amplification product of the wild-type template nucleic acid was detected based on the fluorescence emission detected;

identifying, using the one or more processors, a second cluster of data points as wild-type data points, the wild-type data points corresponding to a second set of the plurality of reaction volumes in which amplified product of the wild-type template nucleic acid was detected based on the fluorescence emission detected;

estimating, using the one or more processors, a first coordinate of the cluster plot of data points as a center of the first cluster of data points and a second coordinate of the cluster plot as a center of the second cluster of data points;

determining, using the one or more processors, for each data point of the cluster plot, a first probability of belonging to the first cluster of data points based on a distance of the data point from the first coordinate;

determining, using the one or more processors, for each data point of the cluster plot, a second probability of belonging to the second cluster of data points based on a distance of the data point from the second coordinate;

determining, using the one or more processors, for each data point of the cluster plot, a third probability of belonging to either of the first cluster of data points or the second cluster of data points based on the first probability and the second probability;

comparing, using the one or more processors, the third probability for each data point of the cluster plot to a probability threshold;

based on the comparing, identifying, using the one or more processors, one or more data points of the cluster plot of data points, as one or more false positive data points not belonging to either the first cluster of data points or the second cluster of data points;

establishing, using the one or more processors, a limit of detection for the biological analysis system configured to detect rare target nucleic acid based on information from identifying the one or more false positive data points; and identifying, using the one or more processors, rare target nucleic acid in a test biological sample based on data points obtained from fluorescence emission, detected by the analytical instrument, from a plurality of reaction volumes partitioned from the test biological sample and subjected to a second PCR assay configured to amplify the rare target nucleic acid, wherein the second PCR assay uses the second fluorescence dye as a label for the detecting, and wherein the data points exceed the established limit of detection.

6. The system of claim 5, wherein the memory further comprises instructions for determining a measure of spread between the estimated first and second coordinates of the centers of the first and second clusters of data points, wherein determining the third probability is further based on the determined spread.

7. The method of claim 1, wherein the second fluorescence dye comprises a label for detection of the rare target nucleic acid.

8. The method of claim 1, wherein establishing the limit of detection comprises normalizing the one or more false positive data points.

9. The method of claim 1, further comprising performing the PCR assay on the control biological sample containing the wild-type template nucleic acid.

10. The method of claim 9, further comprising detecting fluorescence emission from the first fluorescence dye.

11. The method of claim 1, wherein the first fluorescent dye comprises VIC.

12. The method of claim 1, wherein the plurality of reaction volumes are disposed in an array.

13. The method of claim 12, wherein the array of reaction volumes comprises through-holes in a microfluidic chip.

14. The method of claim 1, wherein the second fluorescence dye comprises FAM.

15. The system of claim 5, further comprising an array of reaction sites configured to receive the plurality of reaction volumes.

16. The system of claim 15, wherein the array of reaction sites comprises through-holes in a microfluidic chip.

17. The system of claim 5, further comprising a display configured to display the cluster plot.

18. The system of claim 5, further comprising the analytical instrument, wherein the analytical instrument is operably coupled to the one or more processors.

* * * * *